US012209895B2

(12) United States Patent
Salu et al.

(10) Patent No.: US 12,209,895 B2
(45) Date of Patent: Jan. 28, 2025

(54) INLET DIVIDERS HAVING A PLURALITY OF ANALYZING AND PRODUCTION APERTURES FOR ANALYZING MULTIPHASE PRODUCTION FLUID AS WELL AS SYSTEMS INCORPORATING THE SAME

(71) Applicant: Saudi Arabian Oil Company, Dhahran (SA)

(72) Inventors: Samusideen Adewale Salu, Ras Tanura (SA); Mohamed A. Soliman, Ras Tanura (SA); Faris Abdullah Alshuaibi, Al-Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 392 days.

(21) Appl. No.: 17/684,726

(22) Filed: Mar. 2, 2022

(65) Prior Publication Data
US 2023/0280196 A1   Sep. 7, 2023

(51) Int. Cl.
*G01F 1/86* (2006.01)
*G01F 1/74* (2006.01)
*G01N 33/28* (2006.01)

(52) U.S. Cl.
CPC .................. *G01F 1/86* (2013.01); *G01F 1/74* (2013.01); *G01N 33/2841* (2013.01); *G01N 33/2847* (2013.01)

(58) Field of Classification Search
CPC ... G01F 1/86; G01F 1/74; G01F 15/06; G01F 15/08; G01N 33/2841; G01N 33/2847; G01N 33/2823
USPC ...................................................... 73/861.04
See application file for complete search history.

(56) References Cited

U.S. PATENT DOCUMENTS

| 2007/0006727 A1* | 1/2007 | Gysling | .................. G01F 1/666 |
| | | | 95/1 |
| 2012/0234103 A1* | 9/2012 | Boschi | ...................... G01F 1/74 |
| | | | 73/861.04 |

* cited by examiner

*Primary Examiner* — Eric S. McCall
*Assistant Examiner* — Timothy P Graves
(74) *Attorney, Agent, or Firm* — DINSMORE & SHOHL LLP

(57) ABSTRACT

A system for analyzing a multiphase production fluid, the system including a pipeline, an inlet divider having a set of analyzing apertures with densitometers and a set of production apertures, a fluidic separation chamber with flowmeters, a pressure control valve, and a fluidic control unit. Each analyzing aperture of the set of analyzing apertures disposed on a vertically-oriented axis of the inlet divider. The pipeline is configured to supply the multiphase production fluid to the inlet divider. The inlet divider is configured to provide an analysis portion of the multiphase production fluid to the set of analyzing apertures. The inlet divider is configured to provide a production portion of the multiphase production fluid to the set of production apertures. The set of analyzing apertures is configured to provide the analysis portion to the fluidic separation chamber.

18 Claims, 4 Drawing Sheets

INLET DIVIDERS HAVING A PLURALITY OF ANALYZING AND PRODUCTION APERTURES FOR ANALYZING MULTIPHASE PRODUCTION FLUID AS WELL AS SYSTEMS INCORPORATING THE SAME

BACKGROUND

The present disclosure relates to the analysis of multiphase production fluids and, more particularly, to the analysis of multiphase flow in the oil and gas industries, where multiphase flow often involves the simultaneous flow of oil, water and gas.

BRIEF SUMMARY

Conventional systems that monitor multiphase flow rates and phase fractions may be limited in their accuracy and/or the operating envelope in the multiphase flows. In particular, systems may suffer from obtaining a representative profile of the multiphase fluid from a multiphase production supply. This may be due to non-uniformity of the multiphase production fluid within a cross-section of a pipeline providing the multiphase production fluid. Accordingly, a need exists for a system which accurately obtains a representative profile of the multiphase fluid from a multiphase production supply prior to testing the multiphase fluid.

According to the subject matter of the present disclosure, a system for obtaining a representative profile of the multiphase fluid from a multiphase production supply is provided by diverting multiphase production fluid from a vertically oriented set of analyzing apertures within the pipeline of the multiphase production In accordance with one embodiment of the present disclosure is directed to a system for analyzing a multiphase production fluid, the system including a pipeline, an inlet divider having a set of analyzing apertures and a set of production apertures, a fluidic separation chamber, a pressure control valve, and a fluidic control unit. Each analyzing aperture of the set of analyzing apertures disposed on a vertically-oriented axis of the inlet divider. The pipeline is configured to supply the multiphase production fluid to the inlet divider. The inlet divider is configured to provide an analysis portion of the multiphase production fluid to the set of analyzing apertures. The inlet divider is configured to provide a production portion of the multiphase production fluid to the set of production apertures. The set of analyzing apertures is configured to provide the analysis portion to the fluidic separation chamber. The fluidic control unit is in communication with the fluidic separation chamber, and the pressure control valve, and is configured to communicate with the pipeline to supply the multiphase production fluid to the inlet divider. The fluidic control unit is further configured to communicate with the pressure control valve to regulate flow of the analysis portion of the multiphase production fluid from the set of analyzing apertures to the fluidic separation chamber. The fluidic control unit is further configured to communicate with the fluidic separation chamber to separate the analysis portion of the multiphase production fluid into a gas phase, an oil phase, and a water phase.

In accordance with another embodiment of the present disclosure, an inlet divider is disclosed for analyzing a multiphase production fluid. The inlet divider having a set of analyzing apertures configured to receive an analysis portion of the multiphase production fluid, a set of outlet tubes in fluid communication with each analyzing aperture of the set of analyzing apertures, and a set of production apertures configured to receive a production portion of the multiphase production fluid. Each analyzing aperture of the analyzing apertures is disposed on a vertically-oriented axis of the inlet divider, thereby capturing a representative profile of the multiphase production fluid. The set of outlet tubes are configured to receive the analysis portion of the multiphase production fluid after interfacing with each analyzing aperture of the set of analyzing apertures.

In accordance with another embodiment of the present disclosure, an inlet divider is disclosed for analyzing a multiphase production fluid. The inlet divider having a set of analyzing apertures configured to receive an analysis portion of the multiphase production fluid and a set of outlet tubes in fluid communication with each analyzing aperture of the set of analyzing apertures. Each analyzing aperture of the analyzing apertures is disposed on a vertically-oriented axis of the inlet divider, thereby capturing a representative profile of the multiphase production fluid. The set of outlet tubes in fluid communication with each analyzing aperture of the set of analyzing apertures and configured to receive the analysis portion of the multiphase production fluid after interfacing with each analyzing aperture of the set of analyzing apertures.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
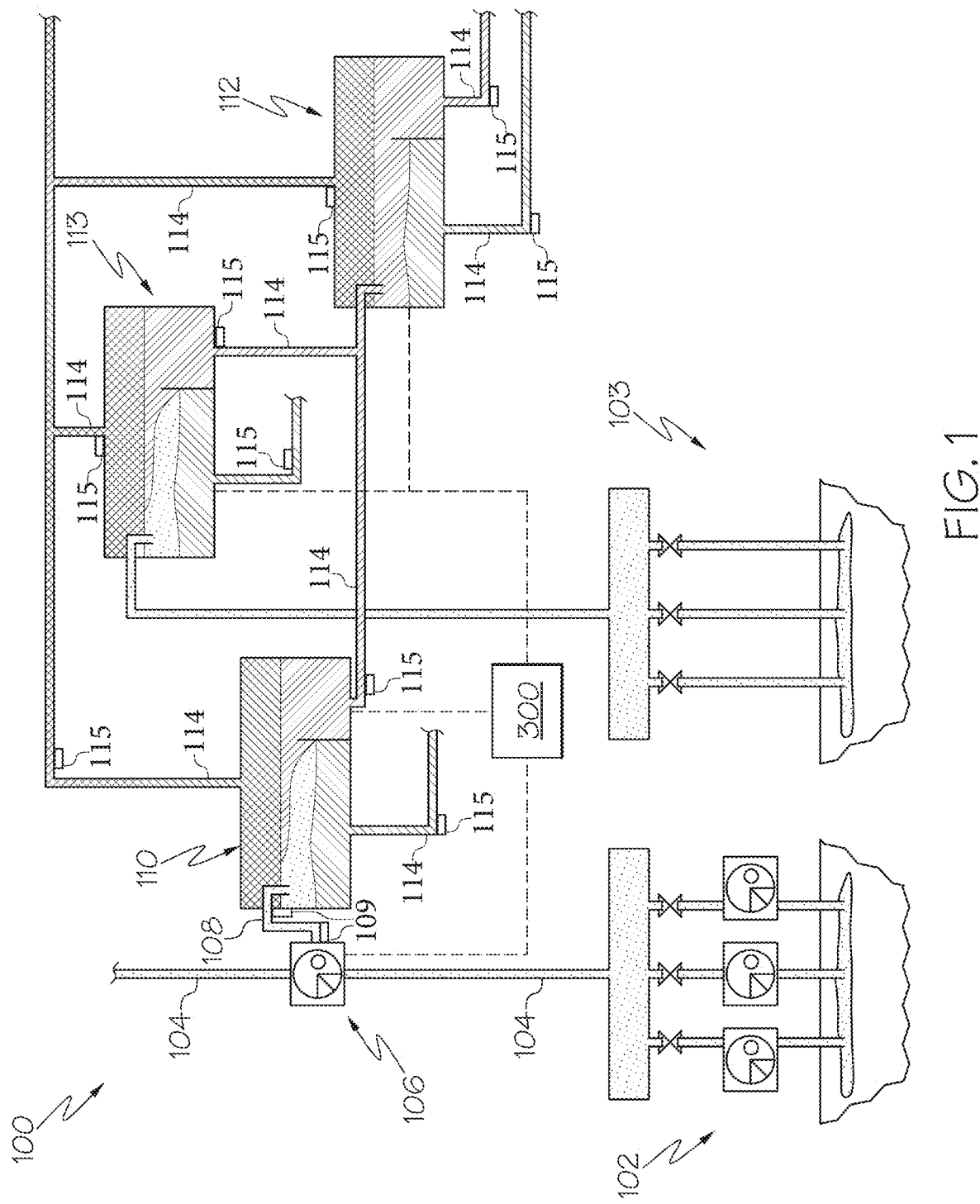
FIG. 1 illustrates systems for analyzing a multiphase production fluid, according to embodiments of the present disclosure.
Figure 4:
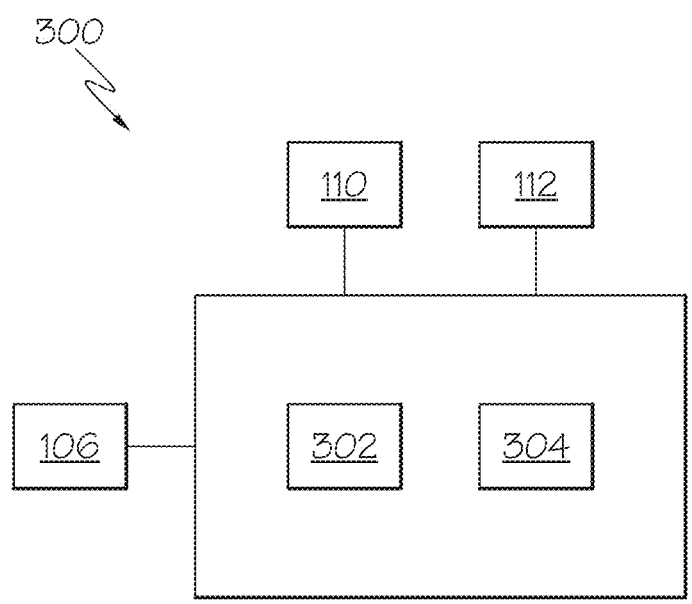
FIG. 4 schematically depicts a control unit for an inlet divider, according to embodiments described in this disclosure.

Referring initially to FIGS. 1 and 4, a system 100 for collecting a representative fluid portion for analyzing a multiphase production is shown, according to embodiments of the present disclosure. The system 100 may include a supply pipeline 104, an inlet divider 106, a separator inlet 108, a fluidic control unit 300, a first fluidic separation chamber 110, and a second fluidic separation chamber 112. The system 100 receives resources from the earth from an oil reservoir 102. The resources may include any of crude oil, gas, oil shale, and any other resources of the like. The oil reservoir 102 is fluidly coupled to the supply pipeline 104 and is configured to provide resources to the supply pipeline 104.

The multiphase production fluid within the supply pipeline 104 may have a non-uniform profile based on its location within the cross-section of the pipeline. This non-uniformity may be a result of varying flow patterns, such as segregated flow, intermittent flow, stratified flow, annular flow, etc. Accordingly, analyzing the multiphase production fluid from one of the non-uniform flow patterns may result in an incorrect analysis of a volume of each phase of the multiphase production fluid.

The supply pipeline 104 is in fluid communication with the inlet divider 106 and is configured to provide resources, such as multiphase production fluid, to the inlet divider 106. As discussed in greater detail herein, the inlet divider 106 is configured to divert a representative portion of the multiphase production fluid from the supply pipeline 104. The representative portion of the multiphase production fluid us a portion of the fluid having an accurate representation of the volume of each phase of the multiphase production fluid.

The inlet divider 106 is configured to separate the multiphase production fluid into at least two portions. The first portion is a production portion of the multiphase production fluid. The production portion is configured to continue to the surface of the earth to be used in production via the supply pipeline 104.

The second portion is an analysis portion of the multiphase production fluid. As discussed in greater detail herein, the analysis portion of the multiphase production fluid is constructed to be a representative portion of the multiphase production fluid. The analysis portion of the multiphase production fluid is configured to be continuously collected over a period of time. This provides live readings of each phase of the multiphase production fluid. In embodiments, the analysis portion of the multiphase production fluid is provided to a mobile testing field or a laboratory for testing.

In embodiments, the analysis portion of the multiphase production fluid is provided to the first fluidic separation chamber 110 via the separator inlet 108. The flow from the inlet divider 106 to the first fluidic separation chamber 110, via the separator inlet 108, may be regulated by a pressure control valve 109 that is communicatively coupled to the fluidic control unit 300.

Although the control unit 300 is described as being a single control unit 300, the use of multiple devices and/or systems to perform the functions described herein is contemplated. The control unit 300 includes a processor 302 communicatively coupled to a memory 304. The control unit 300 may be on site with the system 100, at a wellbore, or at a remote location. Moreover, the several components of the control unit 300 may be distributed among those locations.

The processor 302 may include any processing component(s), such as a central processing unit or the like, configured to receive and execute computer readable and executable instructions stored in, for example, the memory 304. In the embodiments described herein, the computer readable and executable instructions for controlling the inlet divider 106 are stored in the memory 304 of the control unit 300. The memory 304 is a non-transitory computer readable memory. The memory 304 may be configured as, for example and without limitation, volatile and/or nonvolatile memory and, as such, may include random access memory (including SRAM, DRAM, and/or other types of random access memory), flash memory, registers, compact discs (CD), digital versatile discs (DVD), and/or other types of storage components. In the embodiments described herein, the processor 302 of the control unit 300 is configured to provide control signals to (and thereby actuate) portions of the system 100, for example the inlet divider 106, the first fluidic separation chamber 110, and the fluidic separation chamber 112. The control unit 300 may also be configured to receive signals from the inlet divider 106, the first fluidic separation chamber 110, and the fluidic separation chamber 112 and, based on these signals, actuate portions of the system 100.

The pressure control valve 109 may provide and receive signals indicative of a pressure reading of the analysis portion of the multiphase production fluid to the fluidic control unit 300. The fluidic control unit 300 may then provide signals to the pressure control valve 109 to control operation of the pressure control valve 109. In embodiments, the pressure control valve 109 is positioned with the inlet divider 106, the separator inlet 108, or the first fluidic separation chamber 110.

The first fluidic separation chamber 110 is configured to separate the analysis portion of the multiphase production fluid provided by the inlet divider 106. The first fluidic separation chamber 110 may separate the multiphase fluid into its oil phase, water phase, and gas phase. The separation of the multiphase production fluid may be performed using horizontal separation chambers, vertical separation chambers, or any suitable separation chambers. The first fluidic separation chamber 110 is communicatively coupled to the fluidic control unit 300 and is configured to provide signals to the fluidic control unit 300 indicative of a ratio of each phase of the separated analysis portion of the multiphase production fluid.

In embodiments, the analysis portion of the multiphase production fluid may not be completely separated after interfacing with the first fluidic separation chamber 110. In these embodiments, the first fluidic separation chamber 110 is in fluid communication with the second fluidic separation chamber 112 and is configured to provide the analysis portion of the multiphase production fluid to the second fluidic separation chamber 112. The second fluidic separation chamber 112 may then continue the separation process of the analysis portion of the multiphase production fluid. The second fluidic separation chamber 112 is communicatively coupled to the fluidic control unit 300 and is configured to provide signals to the fluidic control unit 300 indicative of a ratio of each phase of the separated analysis portion of the multiphase production fluid. In embodiments, a plurality of fluidic separation chambers are used to further separate the analysis portion of the multiphase production fluid. In these embodiments, the analysis portion of the multiphase production fluid may be placed in differing pressures during the separation process to place the multiphase production fluid to their single-phase states.

In embodiments, the system 100 includes a second oil reservoir 103 fluidly coupled to a third fluidic separation chamber 113. In these embodiments, the second oil reservoir 103 may or may not include an inlet divider. The third fluidic separation chamber 113 may be communicatively coupled to the fluidic control unit 300 and is configured to provide signals to the fluidic control unit 300 indicative of a ratio of each phase of the multiphase production fluid received from the second oil reservoir 103. In embodiments, the third fluidic separation chamber 113 is in fluid communication with the first fluidic separation chamber 110 and the second fluidic separation chamber 112 and is configured to provide to or receive from first fluidic separation chamber 110 and the second fluidic separation chamber 112 phases of the multiphase production fluid.

In embodiments, after interfacing with the fluidic separation chambers, the analysis portion of the multiphase production fluid may be returned to the supply pipeline 104 via pressure boosting devices (ejectors and pumps) and a return pipeline (not shown). In embodiments, the fluidic separation chambers and/or the conduits positioned between the inlet divider 106 and the fluidic separation chambers may include a plurality of sensors (e.g., pressure sensors, temperature sensors, flow meters, density sensors). Each of the plurality of sensors may be communicatively coupled to the fluidic control unit 300.

Figure 2:
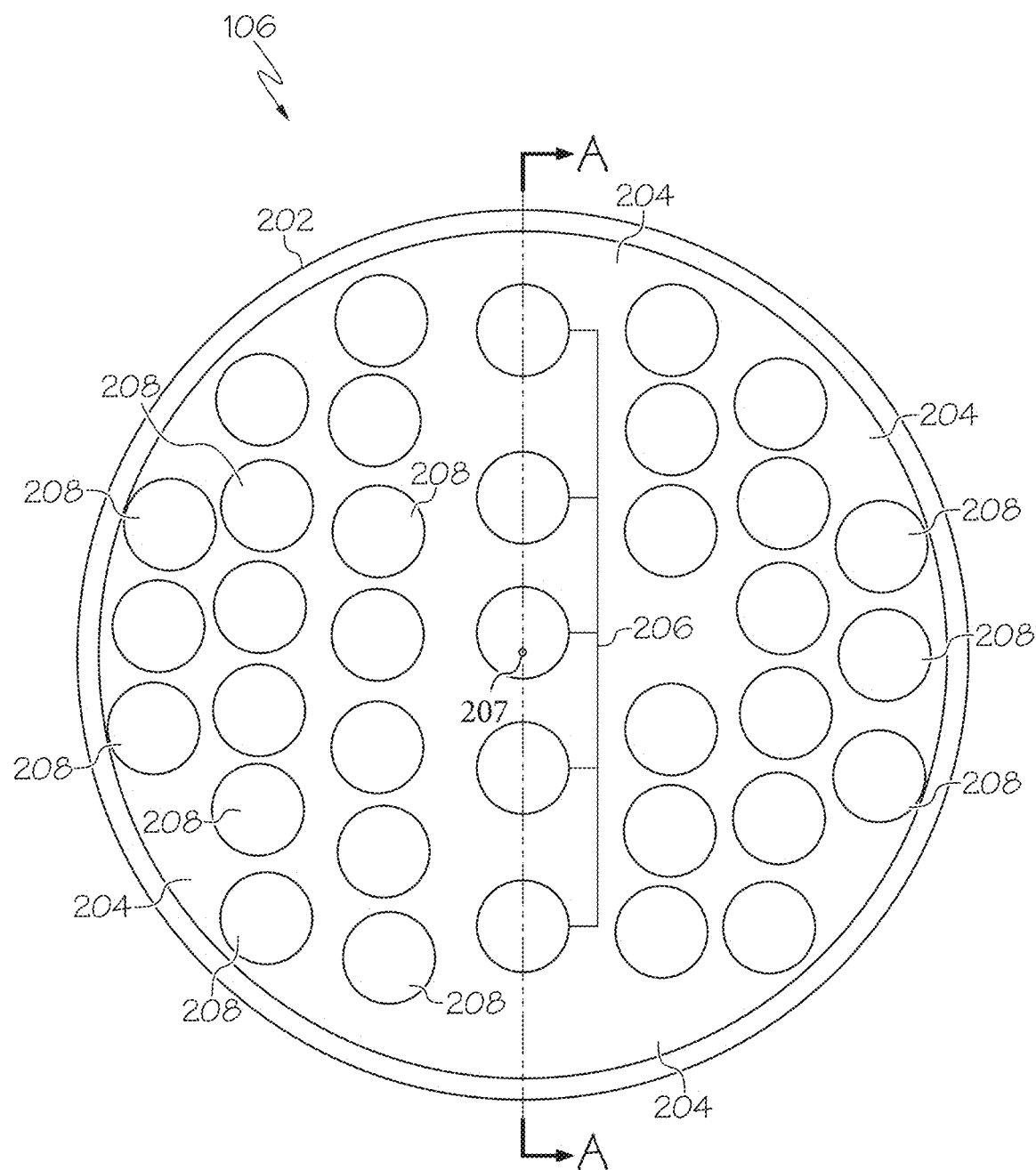
FIG. 2 illustrates an inlet divider for analyzing a multiphase production fluid, according to embodiments of the present disclosure.
Figure 3:
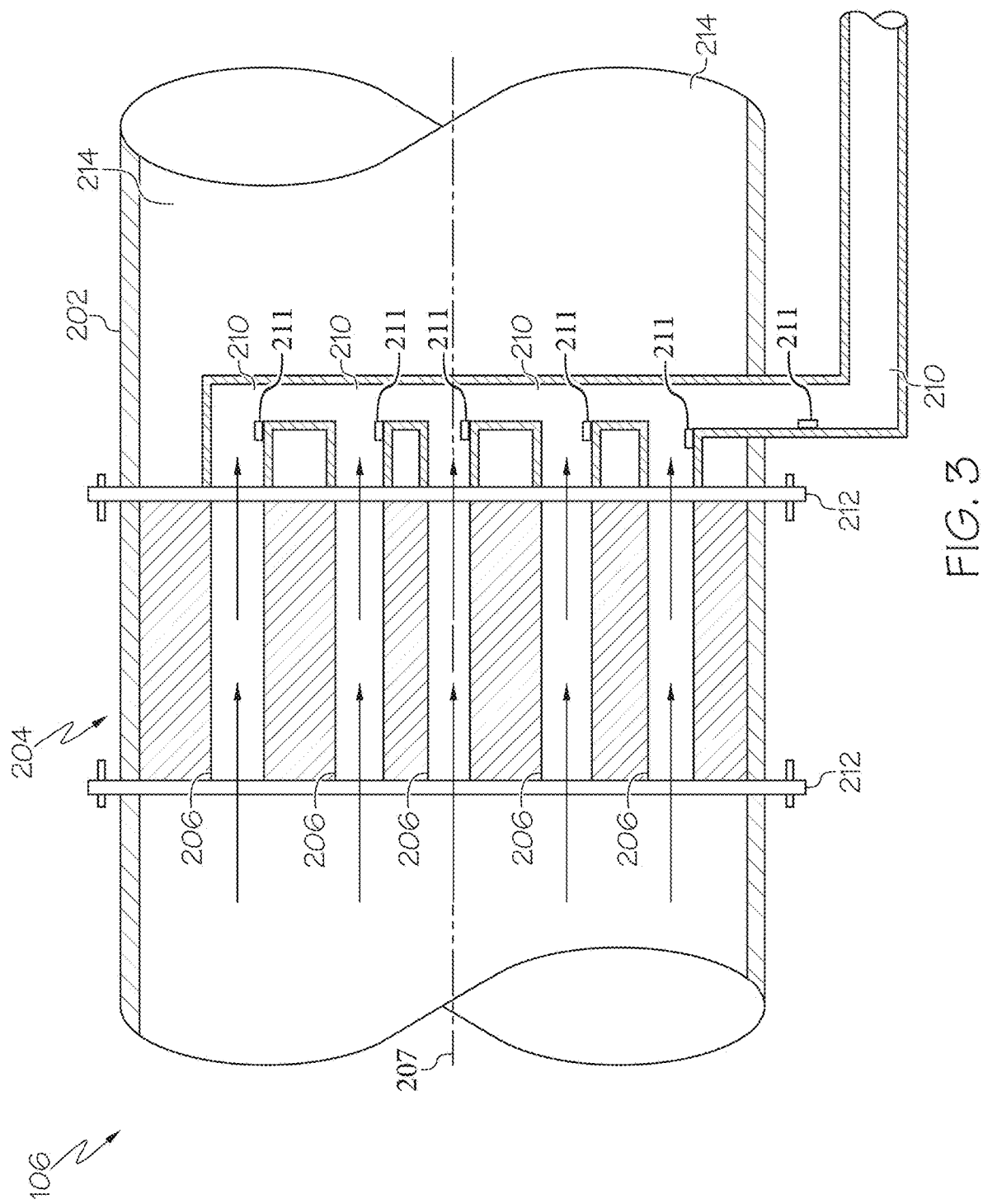
FIG. 3 illustrates a cross-sectional view of the inlet divider in FIG. 2 taken along A-A, according to embodiments of the present disclosure.

Referring now to FIGS. 2 and 3, the inlet divider 106 is shown according to varying embodiments. The inlet divider 106 is configured to separate the multiphase production fluid to the analysis portion of the multiphase production fluid and the production portion of the multiphase production fluid. The inlet divider 106 may include inlet divider piping 202, an inlet divider interface 204, a set of analyzing apertures 206, a set of production apertures 208, a set of outlet tubes 210, interface pins 212, and a production outlet 214.

The inlet divider 106 is encased (e.g., surrounded) by the inlet divider piping 202. The inlet divider piping 202 may be constructed of stainless steel, Corrosion Resistance Alloy (CRA) (e.g., such as like Inconel Metallic Material), or any such material to configured to interface with corrosive fluid.

In embodiments, the inlet divider 106 includes the inlet divider interface 204. The inlet divider interface 204 may be constructed of stainless steel, Corrosion Resistance Alloy (CRA) (e.g., such as like Inconel Metallic Material), or any such material to configured to interface with corrosive fluid. Defined within the inlet divider interface 204 are the set of analyzing apertures 206 and the set of production apertures 208. The inlet divider interface 204 may be secured and/or positioned within the inlet divider piping 202 through the interface pins 212. The interface pins 212 may extend through the entire diameter of the inlet divider piping 202.

The set of production apertures 208 may be through-hole apertures which extend through the inlet divider interface 204. Further, the set of production apertures 208 may be positioned anywhere within the inlet divider piping 202. The multiphase production fluid that enters the set of production apertures 208 become the production portion of the multiphase production fluid. The production portion of the multiphase production fluid continues through the set of production apertures 208 and exits the inlet divider 106 through the production outlet 214. The production outlet 214 may be in fluid communication with the supply pipeline 104 and is configured to provide the production portion of the multiphase production fluid to the supply pipeline 104. The set of production apertures 208 may have any number of production apertures.

The set of analyzing apertures 206 may be through-hole apertures which extend through the inlet divider interface 204. In embodiments, the set of analyzing apertures 206 are positioned along a vertically-oriented axis of the inlet divider 106. The vertically-oriented axis may extend along a center axis 207 of the inlet divider 106. In embodiments, the vertically-oriented axis may be any axis parallel to the center axis 207 of the inlet divider 106. In embodiments, the set of analyzing apertures 206 may be positioned anywhere within the inlet divider piping 202, so that it may divert a representative portion of the multiphase production fluid. For example, the set of analyzing apertures 206 may extend a long a horizontal axis of the inlet divider 106.

In embodiments, the inlet divider 106 may not include the set of production apertures 208 and the inlet divider interface 204. In these embodiments, the set of analyzing apertures 206 divert the analysis portion of the multiphase production fluid. The remaining portion of the multiphase production fluid may then continue to the supply pipeline 104.

The multiphase production fluid which enters the set of analyzing apertures 206 become the analysis portion of the multiphase production fluid. The analysis portion of the multiphase production fluid continues through the set of production apertures 208 and re-enters the supply pipeline 104. The set of production apertures 208 may be any number of production apertures.

In embodiments, each analyzing aperture of the set of analyzing apertures 206 and each production aperture of the set of production apertures 208 define a same cross-sectional area along a length of the inlet divider interface 204. In these embodiments, a flow rate ratio (FRR) may be determined using equation 1. The FRR is a ratio for determining a volume of multiphase production fluid which enters the set of analyzing apertures 206 in comparison to the total volume of the multiphase production fluid.

$$FRR = n_{analyzing\ aperture}/n_{total\ apertures} \qquad \text{Equation 1}$$

In embodiments where the set of production apertures 208 and the set of analyzing apertures 206 define varying cross-sectional areas, the FRR may be calculated by determining a total area of the set of analyzing apertures 206 over the total area of the set of analyzing apertures 206 and the set of production apertures 208 combined.

In embodiments, a flowmeter 115 is positioned on each outlet line 114 emerging from each of the plurality of fluidic separation chambers. Each flowmeter 115 may be communicatively coupled with the fluidic control unit 300 and is configured to provide a signal indicative of a flow reading of each fluid stream line emerging from each of the plurality of fluidic separation chambers. In embodiments, each flowmeter 115 may be positioned within each analyzing aperture for the set of analyzing apertures 206 and each production aperture for the set of production apertures 208.

In embodiments, each flowmeter 115 is positioned within each of the set of outlet tubes 210. A flow rate of the analysis portion of the multiphase production fluid may be determined by the fluidic control unit 300 after receiving readings from each flow meter 115. A total flow rate of the multiphase production fluid may be calculated by using equation 2.

$$\text{flow rate}_{analysis\ portion}/FRR \qquad \text{Equation 2}$$

After calculating the total flow rate, the fluidic control unit 300 may determine a production fluid phase volume fraction data, a production fluid phase flow rate data, or both by utilizing the flow rate of the multiphase production fluid and the oil volume, the water volume, and the gas volume of the multiphase production fluid from the plurality of fluidic separation chambers.

Each analyzing aperture of the set of analyzing apertures 206 is in fluid communication with an outlet tube of the set of outlet tubes 210. The set of outlet tubes 210 receive the the analysis portion of the multiphase production fluid from the set of analyzing apertures 206. As discussed above, the inlet divider 106 may provide the analysis portion of the multiphase production fluid to the separator inlet 108 via the set of outlet tubes 210.

Each outlet tube of the set of outlet tubes 210 may include a densitometer 211 positioned within each outlet tube of the set of outlet tubes 210. Each densitometer 211 may be communicatively coupled to the fluidic control unit 300. Each densitometer 211 may provide a signal indicative of a density reading of each portion of the analysis portion of the multiphase production fluid to the fluidic control unit 300.

For the purposes of describing and defining the present invention, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc. For example, the fluid jetting nozzle 118 may be a plurality of fluid jetting nozzles.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A system for analyzing a multiphase production fluid, the system comprising:
a pipeline;
an inlet divider having a plurality of analyzing apertures, a plurality of production apertures, each analyzing aperture of the plurality of analyzing apertures disposed on a vertically-oriented axis of the inlet divider;
a fluidic separation chamber;
a pressure control valve;
a fluidic control unit;
a plurality of outlet tubes corresponding to and disposed between the plurality of analyzing apertures and an inlet of the fluidic separation chamber; and
a plurality of densitometers, wherein,
the pipeline is configured to supply the multiphase production fluid to the inlet divider,
the inlet divider is configured to provide an analysis portion of the multiphase production fluid to the plurality of analyzing apertures,
the inlet divider is configured to provide a production portion of the multiphase production fluid to the plurality of production apertures,
the plurality of analyzing apertures is configured to provide the analysis portion to the fluidic separation chamber;
each of the plurality of outlet tubes contains one of the plurality of densitometers disposed within, such that the plurality of densitometers are configured to provide a density reading for each portion of the analysis portion;
the fluidic control unit is in communication with the fluidic separation chamber, and
the pressure control valve, and the plurality of densitometers and is configured to:
communicate with the pipeline to supply the multiphase production fluid to the inlet divider,
communicate with the pressure control valve to regulate flow of the analysis portion of the multiphase production fluid from the plurality of analyzing apertures to the fluidic separation chamber,
communicate with the plurality of densitometers to obtain a density reading and to determine a flow pattern of the multiphase production fluid in the pipeline by utilizing the density reading, and
communicate with the fluidic separation chamber to separate the analysis portion of the multiphase production fluid into a gas phase, an oil phase, and a water phase.

2. The system of claim 1, further comprising a flowmeter that is in communication with the fluidic control unit and is configured to provide a flow rate for the analysis portion of the multiphase production fluid to the fluidic control unit.

3. The system of claim 2, wherein:
a flow rate of the multiphase production fluid is determined by the equation $$\frac{\text{flow rate}}{n_{analyzing\ aperture}/n_{total\ apertures}},$$

wherein:
flow rate for the equation is the flow rate for the analysis portion of the multiphase production fluid,
$n_{analyzing\ aperture}$ for the equation is the total number of analyzing apertures, and
$n_{total\ aperture}$ for the equation is the total number of analyzing apertures plus the total number of production apertures.

4. The system of claim 3, wherein the fluidic control unit is configured to determine an oil volume, a water volume, and a gas volume of the multiphase production fluid after separating the analysis portion of the multiphase production fluid into the gas phase, the oil phase, and the water phase.

5. The system of claim 4, wherein a production fluid phase volume fraction data, production fluid phase flow rate data, or both is determined by utilizing the flow rate of the multiphase production fluid and the oil volume, the water volume, and the gas volume of the multiphase production fluid.

6. The system of claim 1, wherein each analyzing aperture of the plurality of analyzing apertures and each production aperture of the plurality of production apertures define a same cross-sectional area along a length of the inlet divider.

7. The system of claim 1, further comprising pressure boosting devices and a return pipeline, wherein the pressure boosting devices and the return pipeline are configured to co-operate to reintroduce the analysis portion of the multiphase production fluid to the pipeline.

8. An inlet divider for analyzing a multiphase production fluid, the inlet divider comprising:
a plurality of analyzing apertures configured to receive an analysis portion of the multiphase production fluid, each analyzing aperture of the plurality of analyzing apertures being disposed on a vertically-oriented axis of the inlet divider, thereby capturing a representative profile of the multiphase production fluid;
a plurality of outlet tubes corresponding to and in fluid communication with the plurality of analyzing apertures, such that the plurality of outlet tubes are configured to receive the analysis portion of the multiphase production fluid from the plurality of analyzing apertures;
a plurality of production apertures configured to receive a production portion of the multiphase production; and
a plurality of densitometers, wherein each of the plurality of outlet tubes contains one of the plurality of densitometers disposed within, such that the plurality of densitometers are configured to provide a density reading for each portion of the analysis portion.

9. The inlet divider of claim 8, further comprising a flowmeter configured to determine a flow rate of the analysis portion of the multiphase production fluid.

10. The inlet divider of claim 9, wherein:
a flow rate of the multiphase production fluid is determined by the equation $$\frac{\text{flow rate}}{n_{analyzing\ aperture}/n_{total\ apertures}},$$

wherein:
flow rate for the equation is the flow rate for the analysis portion of the multiphase production fluid,
$n_{analyzing\ aperture}$ for the equation is the total number of analyzing apertures, and
$n_{total\ apertures}$ for the equation is the total number of analyzing apertures plus the total number of production apertures.

11. The inlet divider of claim 8, wherein each analyzing aperture of the plurality of analyzing apertures and each production aperture of the plurality of production apertures define a same cross-sectional area along a length of the inlet divider.

12. The inlet divider of claim 8, wherein the inlet divider is configured such that the analysis portion of the multiphase production fluid is reintroduced with the production portion of the multiphase production fluid downstream of the inlet divider.

13. The inlet divider of claim 9, wherein:
the inlet divider is in fluid communication with a fluidic separation chamber;
the inlet divider is configured to provide the analysis portion of the multiphase production fluid to the fluidic separation chamber; and
the fluidic separation chamber is configured to determine an oil volume, a water volume, and a gas volume of the multiphase production fluid after separating the analysis portion of the multiphase production fluid into a gas phase, an oil phase, and a water phase.

14. The inlet divider of claim 13, wherein a production fluid phase volume fraction data, production fluid phase flow rate data, or both is determined by utilizing the flow rate of the multiphase production fluid and the oil volume, the water volume, and the gas volume of the multiphase production fluid.

15. An inlet divider for analyzing a multiphase production fluid, the inlet divider oriented around a center axis and comprising:
a plurality of analyzing apertures configured to receive an analysis portion of the multiphase production fluid, each analyzing aperture of the plurality of analyzing apertures being disposed on a vertically-oriented axis of the inlet divider parallel to the center axis, thereby capturing a representative profile of the multiphase production fluid; and
a plurality of outlet tubes corresponding to and in fluid communication with the plurality of analyzing apertures, such that the plurality of outlet tubes are configured to receive the analysis portion of the multiphase production fluid from the plurality of analyzing apertures, and wherein:
one of the plurality of analyzing apertures extends along the center axis.

16. The inlet divider of claim 15, further comprising a plurality of production apertures configured to receive a production portion of the multiphase production fluid.

17. The inlet divider of claim 15, wherein:
a flow rate of the multiphase production fluid is determined by the equation $$\frac{\text{flow rate}}{n_{analyzing\ aperture}/n_{total\ apertures}},$$

wherein:
flow rate for the equation is the flow rate for the analysis portion of the multiphase production fluid,
$n_{analyzing\ aperture}$ for the equation is the total number of analyzing apertures, and
$n_{total\ apertures}$ for the equation is the total number of analyzing apertures plus the total number of production apertures.

18. The inlet divider of claim 15, wherein the inlet divider further comprises a plurality of densitometers, each of the plurality of densitometers:
disposed within one of the plurality of outlet tubes, and providing a density reading for each portion of the analysis portion.

* * * * *